(12) United States Patent
Owen (10) Patent No.: US 9,861,453 B2
(45) Date of Patent: Jan. 9, 2018

(54) BRACKET EXTENSION SYSTEM

(71) Applicant: Brandon Owen, Fort Collins, CO (US)

(72) Inventor: Brandon Owen, Fort Collins, CO (US)

( * ) Notice: Subject to any disclaimer, the term of this patent is extended or adjusted under 35 U.S.C. 154(b) by 0 days.

(21) Appl. No.: 15/627,226

(22) Filed: Jun. 19, 2017

(65) Prior Publication Data

US 2017/0281316 A1 Oct. 5, 2017

Related U.S. Application Data (63) Continuation-in-part of application No. 14/504,325, filed on Oct. 1, 2014.

(60) Provisional application No. 61/886,461, filed on Oct. 3, 2013.

(51) Int. Cl.
| | |
|---|---|
| *A61C 3/00* | (2006.01) |
| *A61C 7/14* | (2006.01) |
| *A61C 7/16* | (2006.01) |
| *A61C 7/18* | (2006.01) |

(52) U.S. Cl.
CPC ............ *A61C 7/141* (2013.01); *A61C 7/145* (2013.01); *A61C 7/148* (2013.01); *A61C 7/16* (2013.01); *A61C 7/18* (2013.01)

(58) Field of Classification Search
CPC .......................... A61C 7/14–7/306; A61C 7/12
USPC ............................................ 433/8–17, 22–24
See application file for complete search history.

(56) References Cited

U.S. PATENT DOCUMENTS

| | | | | |
|---|---|---|---|---|
| 2,716,283 A | * | 8/1955 | Atkinson ............... | A61C 7/12 433/14 |
| 3,087,244 A | * | 4/1963 | Huettner ................ | A61C 7/12 433/14 |
| 3,250,003 A | * | 5/1966 | Collito .................. | A61C 7/141 433/9 |
| 4,068,379 A | * | 1/1978 | Miller ................... | A61C 7/16 433/9 |
| 4,077,126 A | * | 3/1978 | Pletcher ................ | A61C 7/285 433/10 |
| 4,243,386 A | * | 1/1981 | Kawaguchi ............ | A61C 7/16 433/9 |
| 4,494,931 A | * | 1/1985 | Wildman ............... | A61C 7/12 433/3 |
| 4,551,094 A | * | 11/1985 | Kesling ................. | A61C 7/30 433/17 |

(Continued)

FOREIGN PATENT DOCUMENTS

| | | |
|---|---|---|
| WO | 2015/042481 | 3/2015 |
| WO | 2015/051224 | 4/2015 |

OTHER PUBLICATIONS

U.S. Appl. No. 661/886,461, filed Oct. 3, 2013.
U.S. Appl. No. 14/504,325, filed Oct. 1, 2014.
U.S. Appl. No. 61/886,461, filed Oct. 3, 2013.

*Primary Examiner* — Stephen R Crow
*Assistant Examiner* — Garrett Atkinson
(74) *Attorney, Agent, or Firm* — Craig R. Miles; CR Miles P.C.

(57) ABSTRACT

An orthodontic bracket extension system for orthodontic braces, the orthodontic bracket extension system including a plurality of bracket base extensions each having an aperture in which a corresponding one of a plurality of bracket base can be disposed to increase a bracket bonding surface area for greater securement of each of the plurality of brackets to each of a corresponding plurality of teeth.

6 Claims, 7 Drawing Sheets

(56) References Cited

U.S. PATENT DOCUMENTS

| | | | | |
|---|---|---|---|---|
| 4,565,526 | A * | 1/1986 | Kawata | A61C 7/30 433/14 |
| 4,889,485 | A * | 12/1989 | Iida | A61C 7/16 433/9 |
| 4,948,366 | A * | 8/1990 | Horn | A61C 7/12 156/226 |
| 5,098,288 | A * | 3/1992 | Kesling | A61C 7/12 433/9 |
| 5,248,257 | A * | 9/1993 | Cannon | A61C 7/287 433/14 |
| 5,263,859 | A * | 11/1993 | Kesling | A61C 7/12 433/24 |
| 5,464,347 | A * | 11/1995 | Allesee | A61C 7/12 433/16 |
| 5,782,631 | A * | 7/1998 | Kesling | A61C 7/287 433/11 |
| 6,206,690 | B1 * | 3/2001 | Vargas | A61C 7/14 433/8 |
| 6,247,923 | B1 * | 6/2001 | Vashi | A61C 7/287 433/10 |
| 6,371,760 | B1 * | 4/2002 | Zavilenski | A61C 7/16 433/8 |
| 6,685,468 | B1 * | 2/2004 | Kesling | A61C 7/16 433/9 |
| 6,749,426 | B2 * | 6/2004 | Devanathan | A61C 7/16 433/9 |
| 7,033,170 | B2 * | 4/2006 | Cordato | A61C 7/14 433/10 |
| 7,131,836 | B1 * | 11/2006 | Kesling | A61C 5/00 433/9 |
| 7,331,782 | B2 * | 2/2008 | Andreiko | A61C 7/16 433/9 |
| 7,837,466 | B2 * | 11/2010 | Griffith | A61C 7/12 433/10 |
| 8,550,814 | B1 * | 10/2013 | Collins | A61C 7/12 433/17 |
| 8,979,528 | B2 * | 3/2015 | Macchi | A61C 7/14 433/10 |
| 2003/0039938 | A1 * | 2/2003 | Orikasa | A61C 7/287 433/11 |
| 2005/0244774 | A1 * | 11/2005 | Abels | A61C 7/285 433/10 |
| 2007/0259300 | A1 * | 11/2007 | McLaughlin | A61C 7/12 433/8 |
| 2008/0070184 | A1 * | 3/2008 | Farzin-Nia | A61C 7/287 433/9 |
| 2008/0311534 | A1 * | 12/2008 | Farzin-Nia | A61C 7/287 433/11 |
| 2009/0004617 | A1 * | 1/2009 | Oda | A61C 7/02 433/8 |
| 2009/0004619 | A1 * | 1/2009 | Oda | A61C 7/14 433/24 |
| 2010/0173256 | A1 * | 7/2010 | Rodriguez | A61C 7/141 433/10 |
| 2011/0311932 | A1 * | 12/2011 | Parker | A61C 7/12 433/9 |
| 2013/0017506 | A1 * | 1/2013 | Parker | A61C 7/28 433/24 |

* cited by examiner

BRACKET EXTENSION SYSTEM

This United States Patent Application is a continuation-in-part of U.S. patent application Ser. No. 14/504,325, filed Oct. 1, 2014, which claims the benefit of U.S. Provisional Patent Application No. 61/886,461, filed Oct. 3, 2013, each hereby incorporated by reference herein.

I. FIELD OF THE INVENTION

An orthodontic bracket extension system for orthodontic braces, the orthodontic bracket extension system including a plurality of bracket base extensions each having an aperture in which a corresponding one of a plurality of bracket base can be disposed to increase a bracket bonding surface area for greater securement of each of the plurality of brackets to each of a corresponding plurality of teeth.

II. BACKGROUND OF THE INVENTION

Conventional orthodontic brackets have bracket bases which are configured to directly bond to the surface of a tooth. However, particular prescriptions for forces or pressures which transfer from an archwire disposed within the bracket to the bracket can be sufficient to cause the bracket base to detach from the surface of the corresponding tooth.

Accordingly, a need exists for a system which can provide greater adherent forces between the bracket and the tooth surface to eliminate or reduce the occurrence of detachment of the bracket base from the surface of the corresponding tooth.

III. SUMMARY OF THE INVENTION

A broad object of the invention can be to provide a bracket for an orthodontic appliance including one or more of: a bracket base having opposed bracket base first and second surfaces joined at a bracket base periphery which delimits a bracket base surface area of the bracket base first and second surfaces, and a bracket body having a bracket body length disposed between bracket body first and second ends with the bracket body first end coupled to the bracket base second surface and the bracket body second end having an archwire slot configured to receive an archwire of the orthodontic appliance, and a bracket base extension having opposed bracket base extension first and second surfaces joined at a bracket base extension periphery which delimits a bracket base extension surface area of the bracket base extension first and second surfaces, the bracket base extension having an aperture communicating between the bracket base extension first and second surfaces. The bracket base can be secured in the aperture of the bracket base extension to locate the bracket base first surface in relation to the bracket base extension first surface to allow the bracket base first surface and the bracket base extension first surface to fixedly mount to one of a plurality of teeth in a dental arch.

A broad object of a particular embodiment of the invention can be to provide an orthodontic bracket extension system including one or more of: a plurality of brackets of an orthodontic appliance, each of the brackets including a bracket base having opposed bracket base first and second surfaces delimited by a bracket base periphery which defines a bracket base surface area of the bracket base first and second surfaces, and a bracket body having a bracket body length disposed between bracket body first and second ends, the bracket body first end coupled to the bracket base second surface, the bracket body second end terminating in an archwire slot configured to receive an archwire of the orthodontic appliance; each of the plurality of brackets interchangeable in combinations with a plurality of bracket base extensions, each of the bracket base extensions having opposed bracket base extension first and second surfaces delimited by a bracket base extension periphery which defines a bracket base extension surface area, and having an aperture element communicating between the bracket base extension first and second surfaces. A selected one of the plurality of bracket bases can be received in or secured in the aperture of a selected one of the plurality of bracket base extensions to locate the bracket base first surface in relation to the bracket base extension first surface affording a configuration of the bracket base first surface and the bracket base extension first surface configured fixedly mounted to one of a plurality of teeth in a dental arch.

Another broad object of a particular embodiment of the invention can be to provide a method of producing an orthodontic bracket extension system, the method including one or more of: obtaining a bracket for an orthodontic appliance, the bracket including a bracket base having opposed bracket base first and second surfaces delimited by a bracket base periphery which defines a bracket base surface area of the bracket base first and second surfaces and a bracket body having a bracket body length disposed between bracket body first and second ends, the bracket body first end coupled to the bracket base second surface, the bracket body second end terminating in an archwire slot configured to receive an archwire of the orthodontic appliance; obtaining a bracket base extension having opposed bracket base extension first and second surfaces delimited by a bracket base extension periphery which defines a bracket base extension surface area of the bracket base extension first and second surfaces having an aperture communicating between the bracket base extension first and second surfaces which can receive or secure the bracket base to locate the bracket base first surface in relation to the bracket base extension first surface, whereby the bracket base first surface associated with the bracket base extension first surface has a configuration which can be fixedly mounted to one of a plurality of teeth in a dental arch.

Another broad object of a particular embodiment of the invention can be to provide a method of using an orthodontic bracket extension system, the method including one or more of: selecting a bracket for an orthodontic appliance, the bracket including a bracket base having opposed bracket base first and second surfaces delimited by a bracket base periphery which defines a bracket base surface area of the bracket base first and second surfaces and a bracket body having a bracket body length disposed between bracket body first and second ends, the bracket body first end coupled to the bracket base second surface, the bracket body second end terminating in an archwire slot configured to receive an archwire of the orthodontic appliance; selecting a bracket base extension having opposed bracket base extension first and second surfaces delimited by a bracket base extension periphery which defines a bracket base extension surface area of the bracket base extension first and second surfaces having an aperture communicating between the bracket base extension first and second surfaces which can receive or secure the bracket base to locate the bracket base first surface in relation to the bracket base extension first surface, whereby the bracket base first surface associated with the bracket base extension first surface has a configuration which can be fixedly mounted to one of a plurality of teeth in a dental arch, disposing or securing the bracket base in the aperture of the bracket base extension; and fixedly mounting the bracket base disposed or secured in the aperture of the bracket base to the tooth in the dental arch.

Naturally, further objects of the invention are disclosed throughout other areas of the specification, drawings, and claims.

V. DETAILED DESCRIPTION OF THE INVENTION

Figure 1:
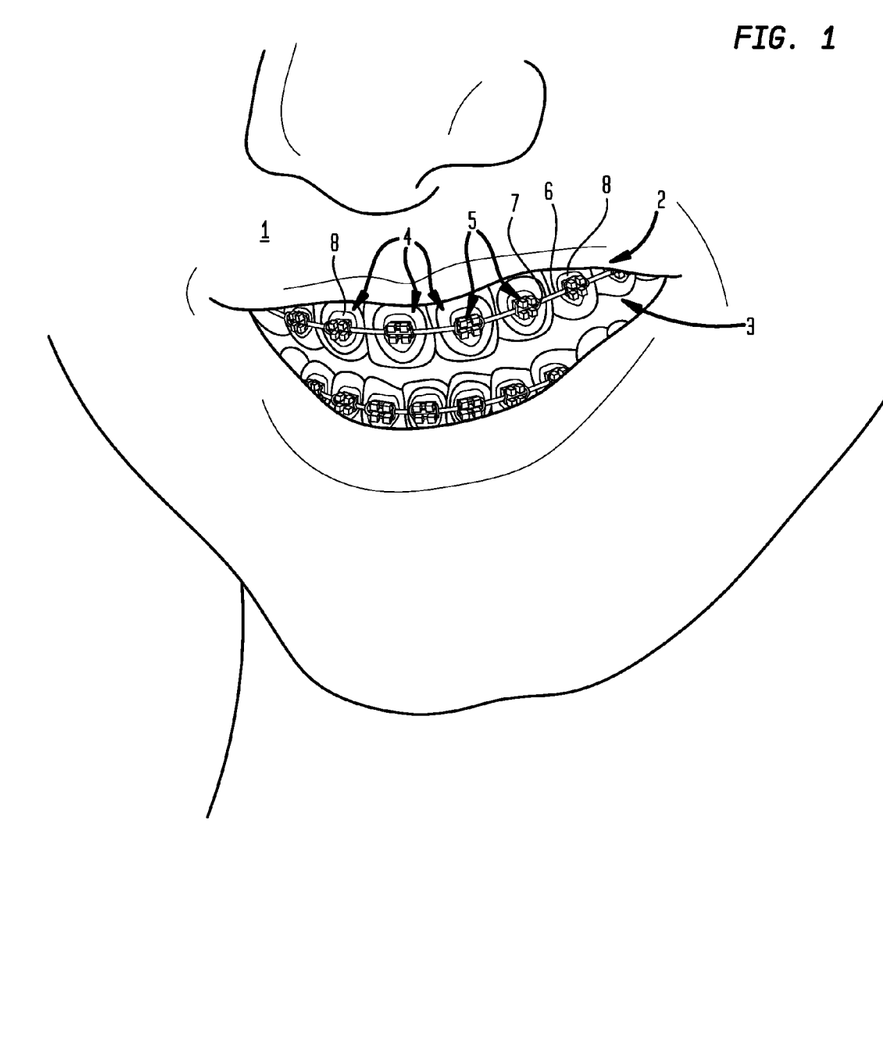
FIG. 1 is an illustration of a particular embodiment of the orthodontic bracket extension system.

Now referring primarily to FIG. 1, embodiments of an orthodontic bracket extension system (1) can be utilized for orthodontic treatment performed by fixing an orthodontic appliance (2) to a plurality of teeth (3). Typically, but not necessarily, the orthodontic bracket extension system (1) includes one or more bracket base extensions (4), a plurality of brackets (5), an archwire (6), and a ligature (7). As shown in the illustrative examples of FIG. 3A, each bracket (5) can have a bracket base (8) which can be received or secured in an aperture (9) communicating between opposed bracket base extension first and second surfaces (10)(11) of the bracket base extension (4). As to particular embodiments, the bracket base (8) can mounted to the surface of a tooth (3) and the bracket base extension (4) subsequently mounted to the tooth (3) with the bracket base (8) disposed in the aperture (9) of the bracket base extension (4), or the bracket base (8) secured within the aperture (9) of the bracket base extension (4) can be mounted as one-piece to the tooth (3). A plurality of brackets (5) correspondingly mounted to a plurality of teeth (3) can be intercoupled by the archwire (6), and the ligature (7) can be used to retain the archwire (6) in association with the plurality of brackets (5). The archwire (6) can generate external forces which can be transferred to the bracket base (8) and the bracket base extension (4) to urge the teeth (3) toward a targeted position or orientation over a period of time. Accordingly, the orthodontic appliance (2) can be utilized to correct maloccused teeth (3).

Figure 2A:
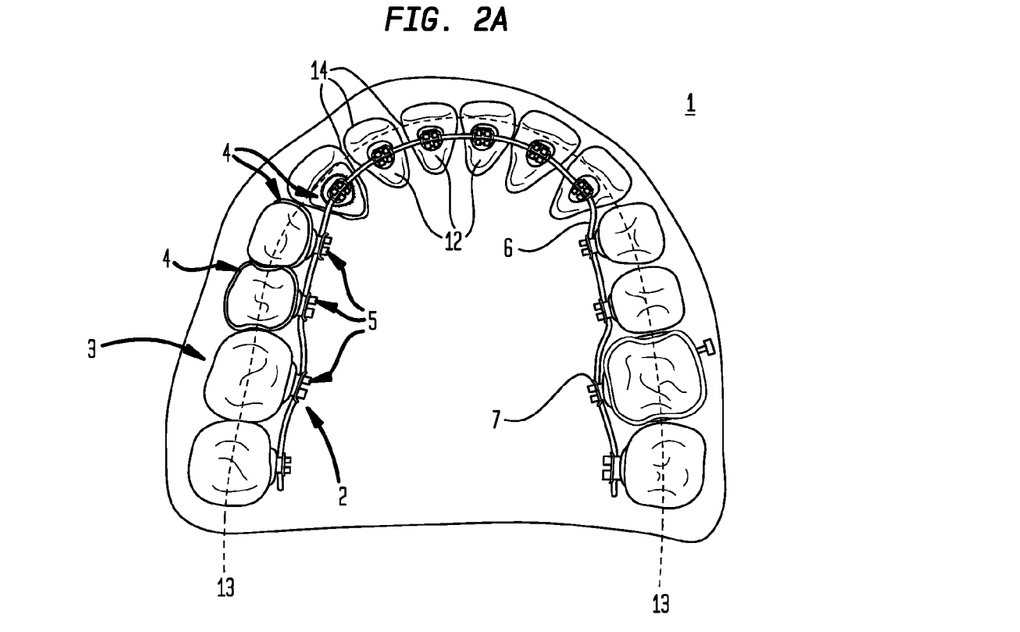
FIG. 2A is an illustration of a particular embodiment of the orthodontic bracket extension system mounted to lingual surfaces of a plurality of teeth.

Now referring primarily to FIG. 2A, as to particular embodiments, the orthodontic bracket extension system (1) can include one or more bracket base extensions (4) which can be mounted to the lingual surfaces (12) of respective teeth (3) around a dental arch (13), whereby the archwire (6) intercoupling the plurality of brackets (5) which in whole or in part can be secured in in the aperture (9) of a corresponding one or more bracket base extensions (4) extends around the lingual surfaces (12) of the teeth (3).

Figure 2B:
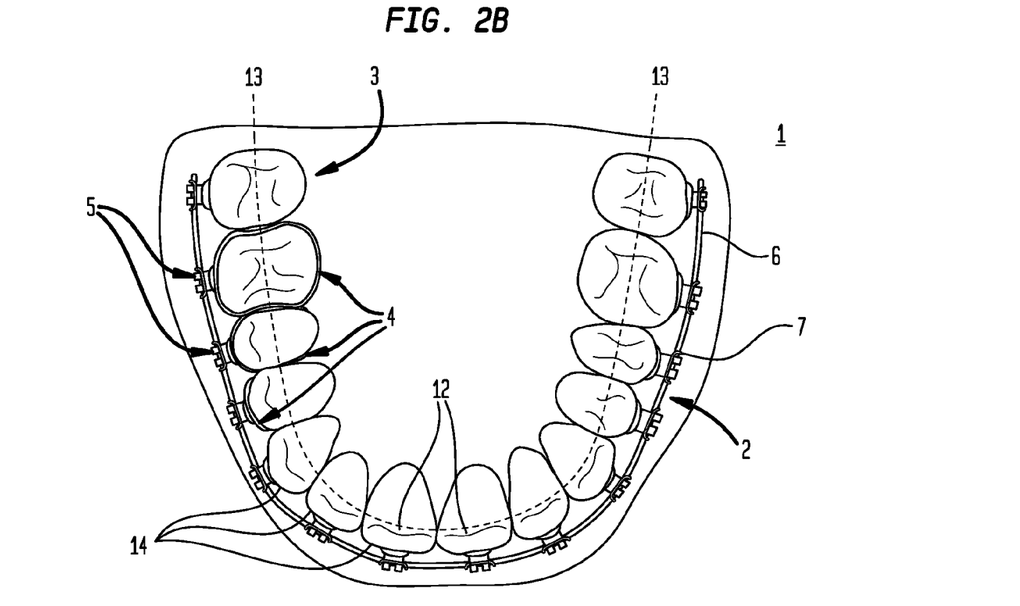
FIG. 2B is an illustration of a particular embodiment of the orthodontic bracket extension system mounted to facial surfaces of a plurality of teeth.

Now referring primarily to FIG. 2B, as to particular embodiments, the orthodontic bracket extension system (1) can include one or more bracket base extensions (4) which can be mounted to the facial surfaces (14) of respective teeth (3) around the dental arch (13), whereby the archwire (6) intercoupling the plurality of brackets (5) which in whole or in part can be secured in the apertures (9) of a corresponding one more bracket base extensions (4) extends around the facial surfaces (14) of the teeth (3).

Now referring primarily to FIG. 3A through FIG. 3K, the orthodontic bracket extension system (1) can include a plurality of brackets (5) of an orthodontic appliance (2) and a plurality of bracket base extensions (4). Each of the brackets (5) can include a bracket base (8) having opposed bracket base first and second surfaces (15)(16) delimited by a bracket base periphery (17) which defines a bracket base surface area (18) of the bracket base first and second surfaces (15)(16). Each of the brackets (5) can further include a bracket body (19) having a bracket body length (20) disposed between bracket body first and second ends (21)(22). The bracket body first end (21) can be coupled to the bracket base second surface (16). The bracket body second end (22) terminates in an archwire slot (23) configured to receive an archwire (6) of the orthodontic appliance (2).

Again referring primarily to FIG. 3A through FIG. 3K, each of the bracket base extensions (4) can have opposed bracket base extension first and second surfaces (10)(11) delimited by a bracket base extension periphery (24) which defines a bracket base extension surface area (25) of the bracket base extension first and second surfaces (10)(11). The bracket base extension first surface (10) can be configured to fixedly mount to a corresponding one of the plurality of teeth (3) in the dental arch (13).

Again referring primarily to FIG. 3A through FIG. 3F, each of the bracket base extensions (4) can include an aperture (9) which communicates between opposed bracket base extension first and second surfaces (10)(11). The aperture (9) can be configured to receive or secure the bracket base (8). The bracket base (8) can be disposed in the aperture (9) of the bracket base extension (4). As shown the illustrative example of FIG. 3D, the bracket base (8) can be disposed in the aperture (9) of the bracket base extension (4) to dispose the aperture periphery (26) in substantially contiguous relation to the bracket base periphery (17) to afford a substantially continuous combination of the bracket base extension first surface (10) and the bracket base first surface (15) configured to fixedly mount to a corresponding one of the plurality of teeth (3) in the dental arch (13).

Figure 3A:
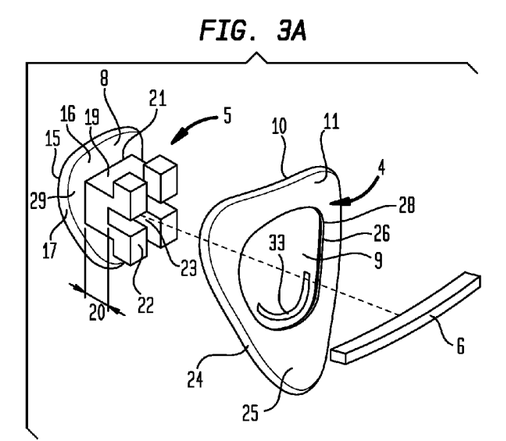
FIG. 3A is an exploded view of a bracket having a bracket base disposable in an aperture of a particular embodiment of a bracket base extension.
Figure 3B:
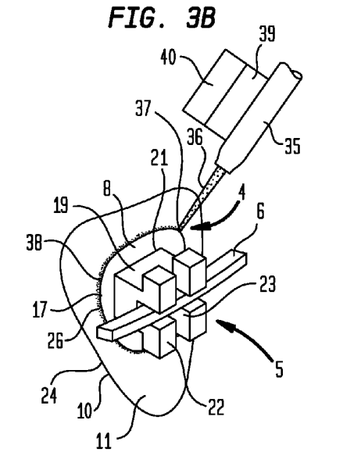
FIG. 3B is perspective second surface elevation view of a particular embodiment of a bracket base disposed in the aperture of a bracket base extension and secured by laser welding at the juncture of the bracket base periphery and the aperture periphery of bracket base extension.
Figures 3C, 3D, 3E:
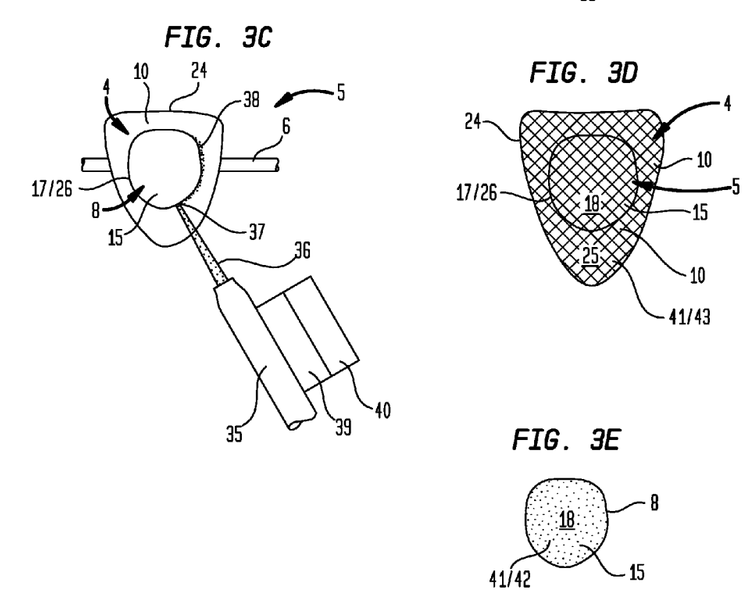
FIG. 3C is first surface elevation view of a particular embodiment of a bracket base disposed in the aperture of a bracket base extension and secured by laser welding at the juncture of the bracket base periphery and the aperture periphery of bracket base extension.
FIG. 3D is first surface elevation view of a particular embodiment of a bracket base disposed in the aperture of a bracket base extension the first surface of the bracket base and the bracket base extension each including mechanical bond enhancement elements.
FIG. 3E is first surface elevation view of a particular embodiment of a bracket base including chemical bond enhancement elements.
Figure 3F:
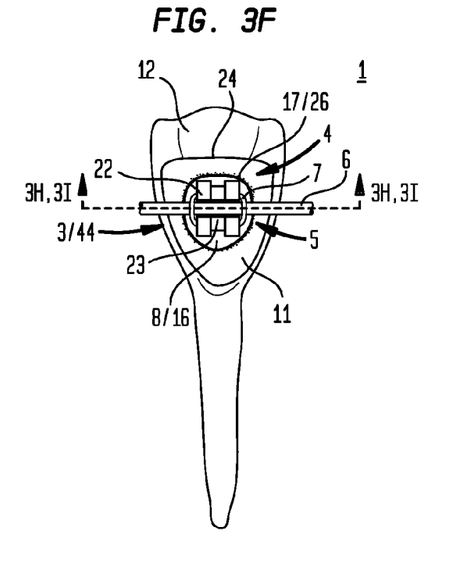
FIG. 3F is a lingual view of an incisor having a particular embodiment of the orthodontic bracket extension system mounted to the lingual surface of the incisor.
Figure 3G:
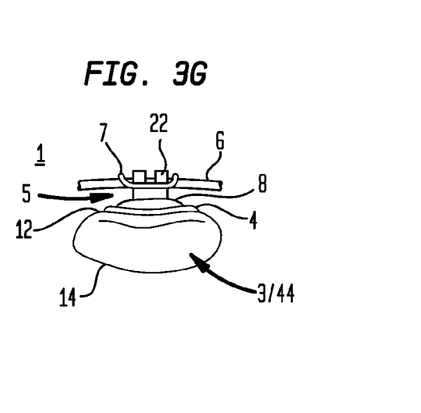
FIG. 3G is an incisal view of an incisor having a particular embodiment of the orthodontic bracket extension system mounted to the lingual surface of the incisor.
Figure 3H:
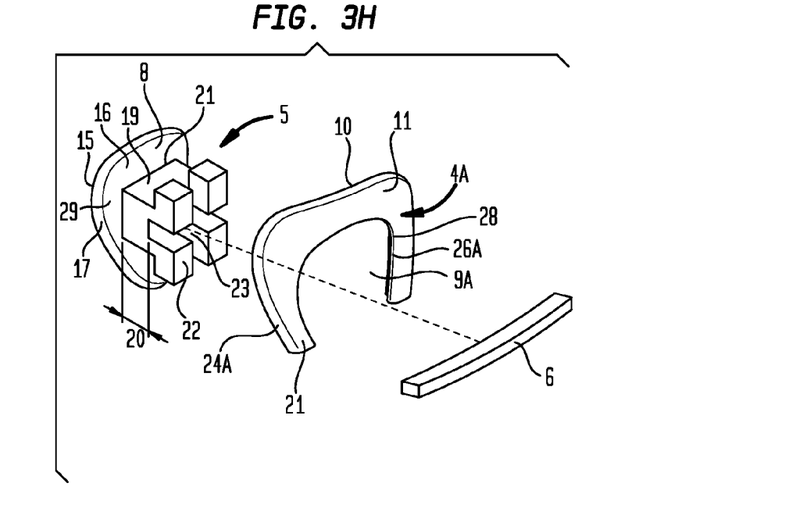
FIG. 3H is an is an exploded view of a bracket having a bracket base disposable in an aperture of a particular embodiment of a bracket base extension.
Figure 3I:
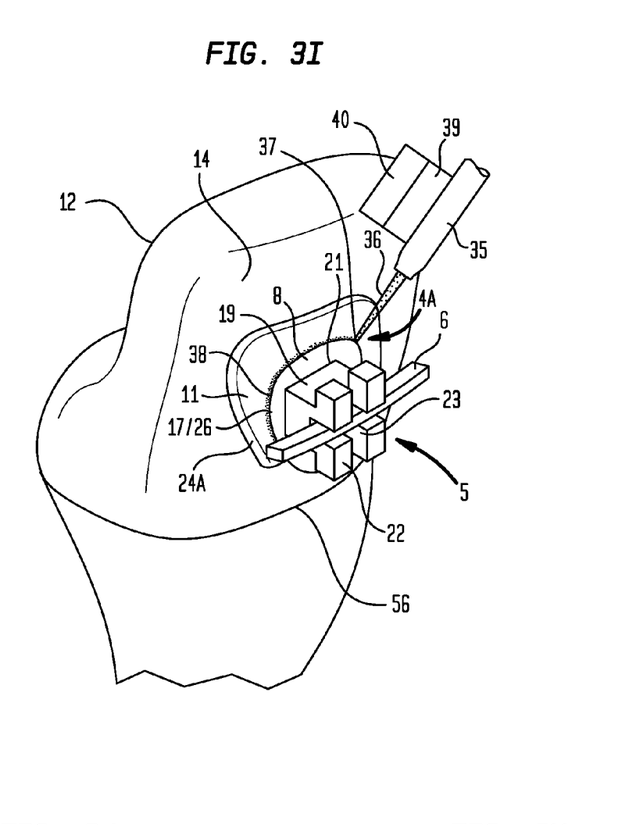
FIG. 3I is perspective view of the particular embodiment of the bracket base extension shown in FIG. 3H mounted to the facial surface of an incisor.
Figure 3J:
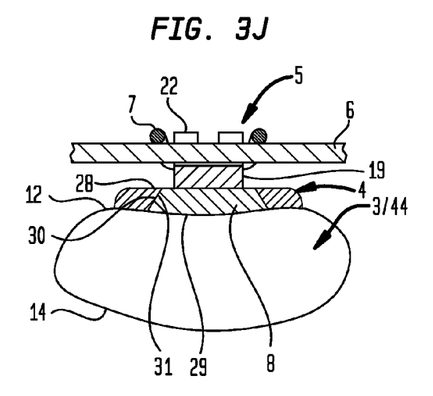
FIG. 3J is an incisal cross section view as shown in FIG. 3F of a particular embodiment of the orthodontic bracket extension system having an aperture margin overlapping a bracket base margin to secure the bracket base in the aperture of the bracket base extension.
Figure 3K:
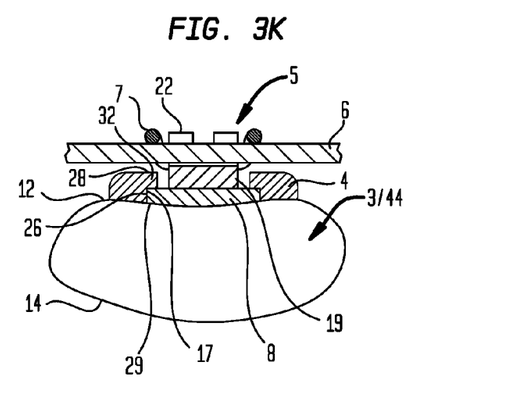
FIG. 3K is an incisal cross section view as shown in FIG. 3F of a particular embodiment of the orthodontic bracket extension system having an aperture margin overlapping a bracket base margin to secure the bracket base in the aperture of the bracket base extension.

Now referring primarily to FIGS. 3A, 3J and 3K, embodiments of the bracket base extension (4) can further include an aperture margin (28) terminating at the aperture periphery (26) and embodiments of the bracket base (8) can further include a bracket base margin (29) terminating at the bracket base periphery (17). The aperture margin (28) can be configured to overlappingly engage the bracket base margin (29). As shown in the illustrative example of FIG. 3J, the aperture margin (28) of the bracket base extension first surface (10) can taper toward the aperture periphery (26) and the bracket base margin (29) of the bracket base second surface (16) can taper toward the bracket base periphery (17). The pair of opposed tapered surfaces (30)(31) can matingly engage when the aperture (9) of the bracket base extension (4) receives or secures the bracket base (8). As shown in the illustrative example of FIG. 3K, the aperture margin (28) and the bracket base margin (29) can each terminate in a corresponding aperture periphery (26) and bracket base periphery (17) which abut in substantially contiguous relation and the bracket base extension (4) can further include a lip (32) projecting from the bracket base second surface (16) which extends in overlapping engagement of the bracket base margin (29) of the bracket base second surface (16). A numerous and wide variety of configurations of the aperture margin (28) and the bracket base margin (29) can be utilized which overlappingly engage to maintain the bracket base (8) in fixed or secured relation to the bracket base extension (4).

Now referring primarily to FIG. 3A, as to particular embodiments, the bracket base (8) can be secured within the aperture (9) of the bracket base extension (4) to afford a one-piece combination of the bracket base (8) and the bracket base extension (4). As to particular embodiments, an amount of bonding adhesive (33) can be provided between the bondable surfaces of the bracket base periphery (17) and the aperture periphery (26). The bonding adhesive (33) can be cured in accordance with the manufacturer's specifications to secure the bracket base (8) in fixed relation to the bracket base extension (4). Any of a wide variety of bonding adhesives (33) can be used to fixedly secure the bracket base (8) within aperture (9) of the bracket base extension (4). Illustrative examples of bonding adhesives (33) can include methacrylate ester monomers (CAS No: 109-16-0); polyacetal (CAS No: 9002-81-7); bisphenol A epichlorhydrin resin (CAS No: 25068-38-6); ABSOLUTE Self-Adhesive Resin Cement, which can be obtained from Centrix, Inc., 770 River Road, Shelton, Conn. 06484, USA; SCOTCHBOND Universal Adhesive, which can be obtained from 3M, 3M Center, St. Paul, Minn. 55144, USA; or the like, or combinations thereof.

Now referring primarily to FIGS. 3B and 3C, as to other particular embodiments, the bracket base (8) and the bracket base extension (4) can both be formed from a weldable metal (34), such as carbon steel, high-strength low-alloy steel, stainless steel, aluminum, titanium, or the like, or combinations thereof. The bracket base (8) disposed in the aperture (9) of the bracket base extension (4) can be fixedly secured by any suitable method of welding which joins materials whether employed at the first or second surfaces of the bracket base extension (4) and bracket base (8) (or both). Illustrative examples include: soldering, arc welding, gas welding, resistance welding, energy beam welding, sold-state welding, or any method of welding which joins materials whether by coalescence or otherwise.

As an illustrative example, the bracket base (8) disposed in the aperture (9) of the bracket base extension (4) can be fixedly secured by laser beam welding (as shown in the illustrative example of FIG. 3B) incorporating a laser (35) having a high power density (on the order of 1 MW/cm$^2$) which results in relatively small heat-affected zones and relatively high heating and cooling rates. A spot size (37) of the laser beam (36) can vary in a range of between about 0.2 millimeters to about 1.0 millimeter; however, the invention need not be so limited, as the spot size (37) can be of lesser or greater size, depending upon the application. The depth of penetration of a laser beam (36) generated by the laser (35) in the bracket base extension (4) can not only be proportional to the amount of power supplied but can also be dependent upon the location of the focal point of the laser beam (36), whereby penetration can be enhanced when the focal point is slightly below the bracket base extension first or second surfaces (10)(11). As to particular embodiments, a continuous or pulsed laser beam (36) can be used, depending upon the application.

As to particular embodiments, in which laser beam welding fixedly secures the bracket base (8) in the aperture (9) of the bracket base extension (4), the bracket base (8) can be positioned in the aperture (9) of the bracket base extension (4) and millisecond-long pulses of the laser beam (36) can generate a weld (38) by moving the laser beam (36) to follow the juncture of the bracket base periphery (17) and the aperture periphery (26) to fixedly secure the bracket base (8) in the aperture (9) of the bracket base extension (4). As to particular embodiments, this can be achieved by manually moving the laser beam (36) along the juncture of the bracket base periphery (17) and the aperture periphery (26). As to other particular embodiments, movement of the laser beam (35) along the juncture of the bracket base periphery (17) and the aperture periphery (26) can be achieved with a mechanical movement apparatus (39), which can be guided in response to input from a laser scanner (40).

Now referring primarily to FIGS. 3D and 3E, the bracket base extension periphery (24) and the aperture periphery (26) can define a bracket base extension surface area (25) which inclusive of the area of the aperture (9) of the bracket base extension first surface (10) can be substantially greater than the bracket base surface area (18) of the bracket base first surface (15). Accordingly, a bracket base extension first surface (10) can afford a bonding surface area which can be substantially greater than the bonding surface area of the bracket base first surface (15), whereby the relatively greater bracket base extension surface area (25) can provide greater adherent forces between the orthodontic bracket extension system (1) and the corresponding teeth (3).

As used herein, the term "substantially greater" means greater than five percent (5%). As an illustrative example, a bracket base extension surface area (25) is substantially greater than a bracket base surface area (18) when the bracket base extension surface area (23) is at least 5% greater than the bracket base surface area (15). As an additional illustrative example, a bracket base extension surface area (23) of at least 10.5 mm$^2$ is substantially greater than a bracket base surface area (15) of 10 mm$^2$, as 10.5 mm$^2$ is at least 5% greater than 10 mm$^2$.

Again referring to FIGS. 3D and 3E, as to particular embodiments, the bracket base extension first surface (10) can further include bond enhancement elements (41) to increase adherent forces between the bracket base extension (4) and the respective lingual or facial tooth surfaces (12) (14). Bond enhancement elements (41) can include chemical bond enhancement elements (42), mechanical bond enhancement elements (43), or a combination thereof. For example, suitable chemical bond enhancement elements (42) can include silane treatment such as described in U.S. Pat. No. 4,948,366, incorporated by reference herein. Suitable mechanical bond enhancement elements (43) can include ridges, pegs, grooves, particles (such as regularly-shaped particles including spheres, rods, or cones, or irregularly-shaped particles such as shards of ceramic material).

In the use of conventional forces and pressures to move the teeth (3) toward targeted positions or orientations over a period of time, greater adherent forces between the orthodontic bracket extension system (1) and the corresponding teeth (3) can eliminate or reduce the occurrence of detachment of one or more bracket base extensions (4) from the corresponding one or more teeth (3). Additionally, greater adherent forces can allow an orthodontic practitioner to prescribe one or more tipping force moments, in-out force moments, or torquing force moments which can be substantially outside of the conventional range of orthodontic mechanics to move one or more teeth (3) in relation to the plurality of teeth (3) of a patient with an elimination or reduction in the occurrence of detachment of one or more bracket base extensions (4) from the corresponding one or more teeth (3).

Embodiments of the bracket base extension (4) can have various configurations adapted for increasing the bracket base extension surface area (25) of the bracket base extension first surface (10), which can be directly bonded to or engaged with the lingual or facial surface (12)(14) of a corresponding tooth (3). As to particular embodiments, the bracket base extension first surface (10) can be configured as a generally planar bracket base extension first surface (10). As to other particular embodiments, the bracket base extension first surface (10) can be configured as an arcuate bracket base extension first surface (10), which can have a concave or convex contour configured to conform to a corresponding convex or concave contour of a mountable tooth surface (12)(14) of a corresponding tooth (3).

Now referring primarily to FIGS. 3F and 3G, as to particular embodiments, the bracket base extension first surface (10) can have a configuration adapted for directly bonding to the lingual surface (12) of a tooth (3), for example an incisor (44), whereby the bracket base extension first surface (10) can have a convex contour configured to conform to a corresponding concave contour of the lingual surface (12) of the incisor (44).

Now referring primarily to FIGS. 3H and 3G, the various bracket base extensions (4), above described can be modified to excise a portion of the bracket base extension (4) to provide a partial bracket base extension (4A), or the partial bracket base extension (4A) can be made in which the bracket base extension periphery (24) and the aperture periphery (26) do not circumferentially enclose the bracket base extension (4) or the aperture (9) but only define a bracket base periphery segment (24A) of the bracket base extension periphery (24) and a aperture periphery segment (26A) of the aperture periphery (26) which define an open sided aperture (9A). As shown in the illustrative examples, of 3H and 3G, the partial bracket base extension (4A) includes an open sided aperture (9A) in which the bracket base (8) can be disposed with a portion of the bracket base periphery (27) engaged with the aperture periphery segment (26A). The bracket base (8) can be fixedly secured in the open sided aperture (9A) as above described for the bracket base (8) fixedly secured in the aperture (9) of other embodiments of the bracket base extension (4). There can be a substantial advantage to the partial bracket base extension (4A) because the bracket base extension periphery segment (24A) and the bracket base aperture periphery segment (26A) can be disposed a distance from the gum line (56).

Figure 4A:
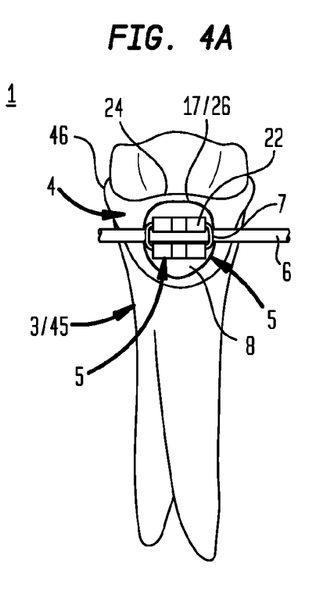
FIG. 4A is a lingual view of a bicuspid (premolar) having a particular embodiment of the orthodontic bracket extension system mounted to the lingual surface of the bicuspid (premolar).
Figure 4B:
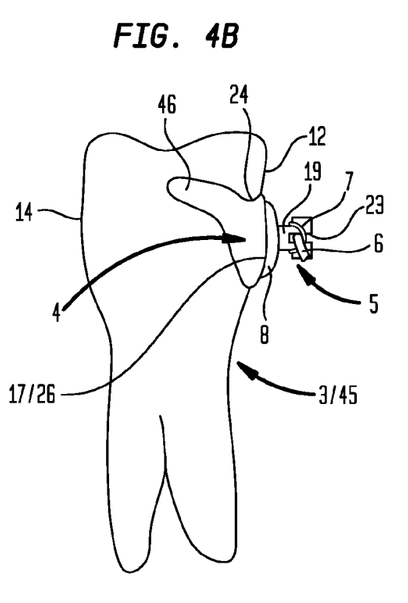
FIG. 4B is a distal view of a bicuspid (premolar) having a particular embodiment of the orthodontic bracket extension system mounted to the lingual surface of the bicuspid (premolar), whereby the bracket base extension includes a partial band.

Now referring primarily FIG. 4A and FIG. 4B, as to particular embodiments, the bracket base extension first surface (10) can have a configuration adapted for directly bonding to the lingual surface (12) of a tooth (3), for example a bicuspid (premolar) (45), whereby the bracket base extension first surface (10) can have a concave contour configured to conform to a corresponding convex contour of the lingual surface (12) of the bicuspid (premolar) (45).

Again referring primarily to FIG. 4A and FIG. 4B, as to particular embodiments, the bracket base extension (4) can further include a partial band (46) adapted to extend, whether mesially or distally, about at least a portion of the tooth (3), for example the bicuspid (premolar) (45), to which the bracket base extension (4) affixes.

As to other particular embodiments, the bracket base extension (4) can further include a partial band (46) adapted to extend about at least a portion of the occlusal surface of the tooth (3) to which the bracket base extension (4) affixes.

Figure 5A:
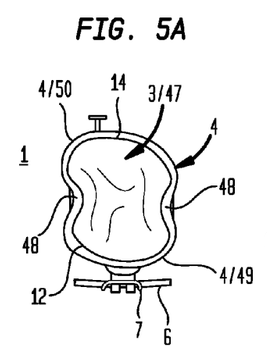
FIG. 5A is an incisal view of a molar having a particular embodiment of the orthodontic bracket extension system mounted to the lingual surface of the molar, whereby the bracket base extension includes a mesial-distal band, the bracket base coupled to the mesial-distal band proximate a mesial-distal band lingual portion.
Figure 5B:
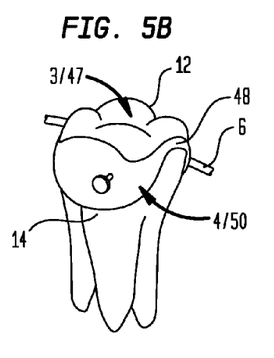
FIG. 5B is a mesiofacial view of a molar having a particular embodiment of the orthodontic bracket extension system mounted to the lingual surface of the molar, whereby the bracket base extension includes a mesial-distal band, the bracket base coupled to the mesial-distal band proximate a mesial-distal band lingual portion.
Figure 5C:
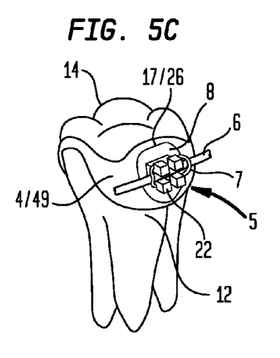
FIG. 5C is distolugual view of a molar having a particular embodiment of the orthodontic bracket extension system mounted to the lingual surface of the molar, whereby the bracket base extension includes a mesial-distal band, the bracket base coupled to the mesial-distal band proximate a mesial-distal band lingual portion.

Now referring primarily to FIG. 5A through FIG. 5C, as to particular embodiments, the bracket base extension (4) can have a configuration adapted for directly bonding to both the lingual and facial surfaces (12)(14) of a tooth (3), for example a molar (47), whereby the bracket base extension (4) can further include a mesial-distal band (48) disposed between mesial-distal band lingual and facial portions (49)(50). The mesial-distal band (48) can be adapted to extend mesially-distally about the molar (47). As to the particular embodiments, the bracket base (8) disposed in the aperture (9) bracket base extension (4) can be coupled to the mesial-distal band (48) proximate the mesial-distal band lingual portion (49). As to other particular embodiments, the bracket base (8) disposed in the aperture (9) of the bracket base extension (4) can be coupled to the mesial-distal band (48) proximate the mesial-distal band facial portion (50).

Figure 6A:
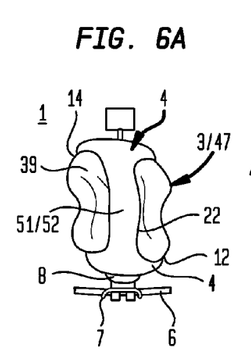
FIG. 6A is an incisal view of a molar having a particular embodiment of the orthodontic bracket extension system mounted to the lingual surface of the molar, whereby the bracket base extension includes a coronal band, the bracket base coupled to the coronal band proximate a coronal band lingual portion.
Figure 6B:
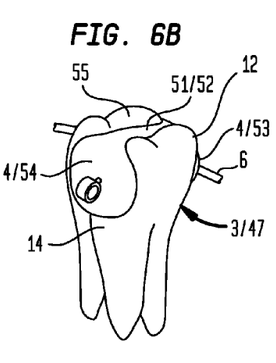
FIG. 6B is meisofacial view of a molar having a particular embodiment of the orthodontic bracket extension system mounted to the lingual surface of the molar, whereby the bracket base extension includes a coronal band, the bracket base coupled to the coronal band proximate a coronal band lingual portion.
Figure 6C:
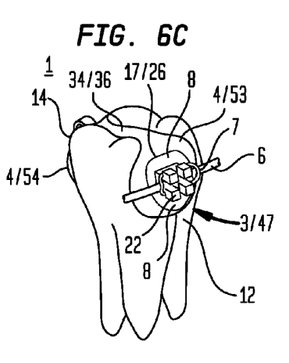
FIG. 6C is distolingual view of a molar having a particular embodiment of the orthodontic bracket extension system mounted to the lingual surface of the molar, whereby the bracket base extension includes a coronal band, the bracket base coupled to the coronal band proximate a coronal band lingual portion.

Now referring primarily FIG. 6A through FIG. 6C, as to particular embodiments, the bracket base extension (4) can have a configuration adapted for directly bonding to both the lingual and facial surfaces (12)(14) of a tooth (3), for example a molar (47), whereby the bracket base extension (4) can further include a coronal band (51) having a coronal band medial portion (52) disposed between coronal band lingual and facial portions (53)(54). The coronal band (51) can be adapted to extend over a coronal portion (55) of the molar (47). As to the particular embodiments, the bracket base extension (4) and corresponding bracket base (8) can be coupled to coronal band (51) proximate the coronal band lingual portion (53). As to other particular embodiments, the bracket base extension (4) and corresponding bracket base (8) can be coupled to coronal band (51) proximate the coronal band facial portion (54).

Again referring primarily to FIGS. 1 and 2A and 2B, and FIGS. 3A through 3I, as to particular embodiments the bracket base (8) or the bracket base extension (4) can be fixedly mounted to one of the plurality of teeth (3) by application of an amount of bonding adhesive (33), as above described, on the bracket base surface area (18) or the bracket base extension surface area (25). The bracket base (8) or the bracket base extension (4) can disposed on the tooth (3) in a predetermined position or with a predetermined orientation, after which excess bonding adhesive (33) can be removed. As to particular embodiments, the bonding adhesive (33) can be cured, for example by using a high-intensity light, to secure the bracket base (8) or the bracket base extension (4) to the surface (12)(14) of the tooth (3). Subsequently, the bracket base (8) or bracket base extension (4) can be correspondingly fixedly mounted to the surface (12)(14) of a tooth (3) disposing bracket base (8) in the aperture (9) of the bracket base extension (4), after which excess bonding adhesive (33) can be removed and the bonding adhesive (33) cured. Upon fixedly mounting the combination of the bracket base (8) and bracket base extension (4) on one of a plurality of teeth (3), as to particular embodiments, the juncture between the aperture periphery (26) and the bracket base periphery (17) can, but need not necessarily, be joined by an amount of additional bonding adhesive (33) or by a weld (38), or laser welding as above described.

Now referring primarily to FIGS. 1, 2A and 2B, and 3B and 3C, as to particular embodiments, the bracket base (8) can be disposed in the aperture (9) of the bracket base extension (4) and fixedly secured to the bracket extension (4) to form a one-piece construct, as above described, in which the base extension first surface (10) and the bracket base first surface (15) form a substantially continuous one-piece surface. The bracket base (8) and bracket base extension (4) can then be fixedly mounted as one-piece to one of the plurality of teeth (3) by application of an amount of bonding adhesive (33) to the combined surfaces of the bracket base extension first surface (10) and the bracket base first surface (15), as above described.

Regardless of the embodiment, upon fixed mounting of the bracket base (8) or the combination of the bracket base (8) and bracket base extension (4) on each one of a plurality of teeth (3), the archwire (6) can be disposed within the archwire slot (23) of the bracket body (19).

A method of producing an orthodontic bracket extension system (1) can include: obtaining (whether by purchase or fabrication) a bracket (5) for an orthodontic appliance (2), the bracket (5) including a bracket base (8) having opposed bracket base first and second surfaces (15)(16) delimited by a bracket base periphery (17) which defines a bracket base surface area (18) of the bracket base first and second surfaces (15)(16) and a bracket body (19) having a bracket body length (20) disposed between bracket body first and second ends (21)(22), the bracket body first end (21) coupled to the bracket base second surface (16), the bracket body second end (22) terminating in an archwire slot (23) configured to receive an archwire (6) of the orthodontic appliance (2). The method can further include obtaining a bracket base extension (4)(whether by purchase of fabrication) having an aperture (9) communicating between opposed bracket base extension first and second surfaces (10)(11) delimited by a bracket base extension periphery (17) which defines a bracket base extension surface area (25) of the bracket base extension first and second surfaces (10)(11). The aperture (9) in the bracket base extension (4) being configured to receive or secure the bracket base (8) in the aperture (9) and having a bracket base extension first surface (25) substantially greater than the bracket base surface area (15) of the bracket base first surface (15). The method can further include disposing the bracket base (8) within the aperture (9) of the bracket base extension (4).

As to particular embodiments, the method can further include fixedly securing the bracket base (8) within the aperture (9) of the bracket base extension (4) to provide the bracket base (8) and the bracket base extension (4) as a one-piece construct which can be bonded to a tooth (3). As to particular embodiments, the bracket base (8) can be secured in the aperture (9) with a bonding adhesive (33). As to other particular embodiments, the method can further include forming the bracket base (8) and the bracket base extension (4) from a weldable metal (34) and fixedly securing the bracket base (8) in the aperture (9) of the bracket base extension (4) by welding.

As to particular embodiments, the method can further include providing the bracket base (8) or the bracket base extension (4) with a chemical bond enhancement element (42). As to other particular embodiments, the method can further include providing the bracket base extension (4) with a mechanical bond enhancement element (43).

As to particular embodiments, components of the orthodontic bracket extension system (1), including the bracket (5) and bracket base extension (4), can each be entirely formed of the same material, or alternatively, can be formed from different materials. As to particular embodiments, components of the orthodontic bracket extension system (1) can be produced from any of a wide variety of materials which can be coupled to a tooth (3) and withstand forces or pressures transferred from the archwire (6) disposed within the bracket (5). By way of illustration, the material can include or consist of: metal, wood, plastic, plastic-like material, acrylic, polyamide, polyester, polypropylene, polyvinyl chloride-based materials, silicone-based materials, or the like, or combinations thereof.

As to particular embodiments, the method can further include configuring the bracket base extension first surface (10) to directly bond to a lingual surface (12) of one of the plurality of teeth (3). As to other particular embodiments, the method can further include configuring the bracket base extension first surface (10) to directly bond to a facial surface (14) of one of the plurality of teeth (3).

As to particular embodiments, the method can further include coupling a partial band (46) to the bracket base extension (4), the partial band (46) configured to extend about at least a portion of a tooth (3) to which the bracket base extension (4) fixedly mounts.

As to particular embodiments, the method can further include coupling a mesial-distal band (48) to the bracket base extension (4), the mesial-distal band (48) configured to extend mesially-distally about a tooth (3) to which the bracket base extension (4) fixedly mounts.

As to particular embodiments, the method can further include coupling a coronal band (51) to the bracket base extension (4), the coronal band (51) configured to extend over a coronal portion (55) of a tooth (3) to which the bracket base extension (4) fixedly mounts.

As to particular embodiments, components of the orthodontic bracket extension system (1) can be produced from any of a wide variety of processes depending upon the application, such as press molding, injection molding, fabrication, machining, printing, three-dimensional printing, or the like, or combinations thereof, as one piece or assembled from a plurality of pieces into an embodiment of a component of the orthodontic bracket extension system (1) or provided as a plurality of pieces for assembly into an embodiment of a component of the orthodontic bracket extension system (1).

A method of using an orthodontic bracket base extension system (1) can include selecting a bracket (5) for an orthodontic appliance (2), the bracket (5) including a bracket base (8) having opposed bracket base first and second surfaces (15)(16) delimited by a bracket base periphery (17) which defines a bracket base surface area (18) of the bracket base first and second surfaces (15)(16) and a bracket body (19) having a bracket body length (20) disposed between bracket body first and second ends (21)(22), the bracket body first end (21) coupled to the bracket base second surface (16), the bracket body second end (22) terminating in an archwire slot (23) configured to receive an archwire (6) of the orthodontic appliance (2).

The method can further include selecting a bracket base extension (4) having opposed bracket base extension first and second surfaces (10)(11) delimited by a bracket base extension periphery (24) which defines a bracket base extension surface area (25) of the bracket base extension first and second surfaces (10)(11) and including an aperture (9) to receive or secure the bracket base (8), the bracket base extension first surface (10) configured to fixedly mount to a tooth (3) in a dental arch (10), whereby the bracket base extension surface area (25) of the bracket base extension first surface (10) is substantially greater than the bracket base surface area (15) of the bracket base first surface (15).

As to particular embodiments, the method can further include fixedly mounting the bracket base (8) to a tooth (3) in the dental arch (10) with an amount of bonding material (33). The method can further include fixedly mounting the bracket base extension (4) to the tooth (3) with an amount of bonding material (33) with the bracket base (8) disposed in the aperture (9) of the bracket base extension (4). The method can further include intercoupling a plurality of brackets (5) mounted to a plurality of teeth (3) by the archwire (6), and further retaining retain the archwire (6) in association with the plurality of brackets (5) with a ligature (7).

As to particular embodiments, in the alternative, the above method includes fixedly securing the bracket base (8) in the aperture (9) of the bracket base extension (4) forming a one-piece construct which the bracket base first surface (15) and the bracket base extension first surface (10) forms continuous or substantially continuous first surfaces (15) (10). The one-piece construct can be fixedly mounted to a tooth (3) in the dental arch (13) with an amount of bonding material (33). The method can further include intercoupling a plurality of brackets (5) mounted to a plurality of teeth (3) by the archwire (6), and further retaining the archwire (6) in association with the plurality of brackets (5) with a ligature (7).

As can be easily understood from the foregoing, the basic concepts of the present invention may be embodied in a variety of ways. The invention involves numerous and varied embodiments of a bracket extension system and methods for making and using such bracket extension systems, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "torque" should be understood to encompass disclosure of the act of "a torquing"—whether explicitly discussed or not—and, conversely, were there effectively disclosure of the act of "torquing", such a disclosure should be understood to encompass disclosure of a "a torque" and even a "means for torquing." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the bracket extension systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. An orthodontic bracket extension system, comprising:
a bracket of an orthodontic appliance said bracket including:
    a bracket base having opposed bracket base first and second surfaces each delimited by a bracket base periphery which defines a bracket base surface area of said bracket base first and second surfaces; and
    a bracket body having a bracket body length disposed between bracket body first and second ends, said bracket body first end coupled to said bracket base second surface, said bracket body second end having an archwire slot configured to receive an archwire of said orthodontic appliance; and
a bracket base extension having opposed bracket base extension first and second surfaces delimited by a bracket base extension periphery which defines a bracket base extension surface area of said bracket base extension first and second surfaces, said bracket base extension having an aperture delimited by an aperture periphery communicating between said bracket base extension first and second surfaces, said bracket base disposable in said aperture of said bracket base extension to locate said bracket base first surface in relation to said bracket base extension first surface to allow said bracket base first surface and said bracket base extension first surface to fixedly mount to one of a plurality of teeth in a dental arch.

2. The system of claim 1, further comprising an aperture margin terminating at said aperture periphery and a bracket base margin terminating at said bracket base periphery, said aperture margin overlappingly engaging said bracket base margin.

3. The system of claim 1, wherein said bracket base fixedly secured in said aperture of said bracket base extension.

4. The system of claim 1, wherein said aperture periphery and said base extension periphery correspondingly define a base extension periphery segment and an aperture periphery segment which define an open sided aperture, said bracket base disposable in said open sided aperture of said bracket base extension.

5. The system of claim 1, further comprising a chemical bond enhancement element coupled to said bracket base first surface or said bracket base extension first surface.

6. The system of claim 1, further comprising a mechanical bond enhancement element coupled to said bracket base first surface or said bracket base extension first surface.

\* \* \* \* \*